United States Patent [19]

Wu

[11] Patent Number: 4,938,768

[45] Date of Patent: Jul. 3, 1990

[54] BONE GAP BRIDGING AND FUSING DEVICE

[75] Inventor: Kent K. Wu, Royal Oak, Mich.

[73] Assignee: Henry Ford Hospital, Detroit, Mich.

[21] Appl. No.: 253,939

[22] Filed: Oct. 5, 1988

Related U.S. Application Data

[63] Continuation of Ser. No. 22,564, Mar. 9, 1987, abandoned, which is a continuation of Ser. No. 764,020, Aug. 9, 1985, abandoned.

[51] Int. Cl.$^5$ .............................. A61F 2/28; A61F 5/04
[52] U.S. Cl. ...................... 623/16; 403/307; 606/60
[58] Field of Search .................... 623/16, 18, 20; 128/92 R, 92 W, 92 Y, 92 YS; 403/306, 307, 300, 292

[56] References Cited

U.S. PATENT DOCUMENTS

| 49,386 | 8/1865 | Cross | 403/307 X |
|---|---|---|---|
| 1,054,812 | 3/1913 | Zierath | 273/80 R |
| 1,265,418 | 5/1918 | Baldwin | 273/80 R |
| 4,401,112 | 8/1983 | Rezian | 128/92 B |
| 4,404,691 | 9/1983 | Buning et al. | 623/20 |
| 4,467,794 | 8/1984 | Maffei et al. | 128/92 B X |
| 4,578,081 | 3/1986 | Hardee et al. | 623/22 |

Primary Examiner—Alan W. Cannon
Attorney, Agent, or Firm—Barnes, Kisselle, Raisch, Choate, Whittemore & Hulbert

[57] ABSTRACT

A bone gap bridging and fusing device for use where large portions of the bone are removed in limbs comprising first and second pin members adapted to be placed in axial openings formed in the opposed remaining bone portions. Each pin member includes a head and the heads of the pin members interengage one another to prevent relative rotation between the pin members. A collar telescopes over the interengaged heads to lock the pin members axially relative to one another.

8 Claims, 4 Drawing Sheets

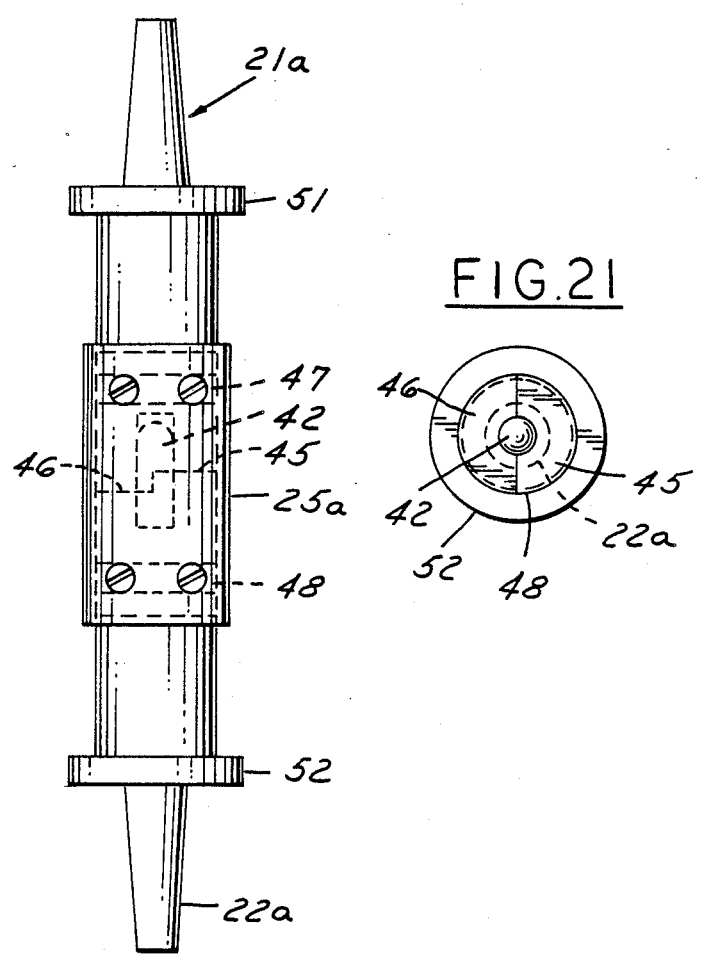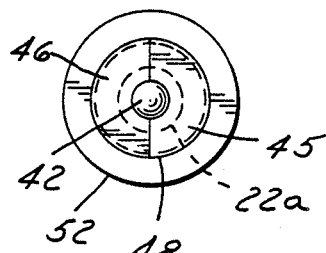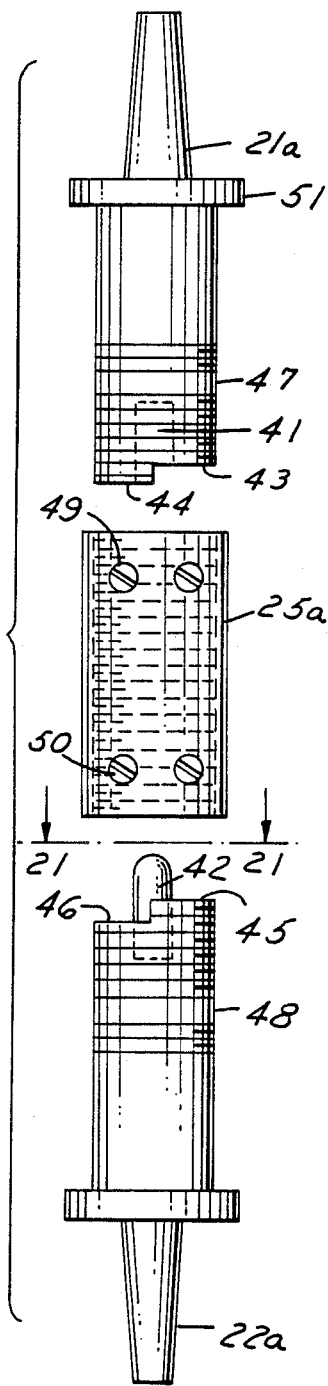

BONE GAP BRIDGING AND FUSING DEVICE

This application is a continuation of application Ser. No. 022,564, filed Mar. 9, 1987, now abandoned, which was, in turn, a continuation of Ser. No. 764,020 filed Aug. 9, 1985, now abandoned.

This invention relates to preservation of limbs of persons who have large portions of the bone of a limb removed.

BACKGROUND AND SUMMARY OF THE INVENTION

In the treatment of persons having cancer in a limb, it is often necessary to remove large portions of the bone. As a result, it has been common to amputate the extremity leaving the person a relative invalid where the limb is a leg. Inasmuch as there is a large gap between the opposed remaining bone portions, it has not been possible to use bone splints such as have been developed to align broken bones which are abutted to one another. Typical patents showing such devices are U.S. Pat. Nos. 2,672,861, 3,744,488, 4,016,874, 4,262,665, and 4,467,794.

Accordingly, among the objectives of the present invention are to provide a bridging device which can be utilized in a limb to span the large gap caused by the removal of large portions of the bone; which device provides strength and stability sufficient to support the person permitting the person to walk thereby permitting the person to be self sufficient.

In accordance with the invention, the bone gap bridging and fusing device for use where large portions of the bone are removed in limbs comprises first and second pin members adapted to be placed in axial openings formed in the opposed remaining bone portions. Each pin member includes a head and the heads of the pin members interengage one another to prevent relative rotation between the pin members. A collar telescopes over the interengaged heads to lock the pin members axially relative to one another.

DESCRIPTION OF THE DRAWINGS

FIG. 19 is an elevational view of a modified form of a device.

FIG. 20 is an exploded view of the device shown in FIG. 19.

FIG. 21 is a view taken along the line 21—21 in FIG. 20.

DESCRIPTION

Figure 1:
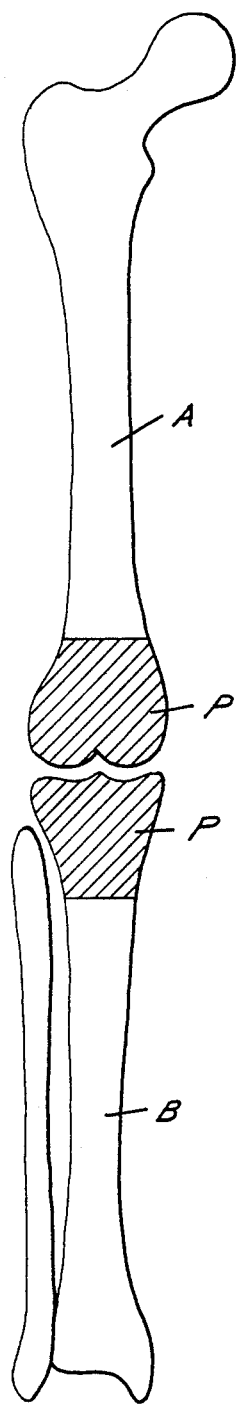
FIG. 1 is a diagrammatic view of a leg which is to have large portions of the bone removed.
Figure 2:
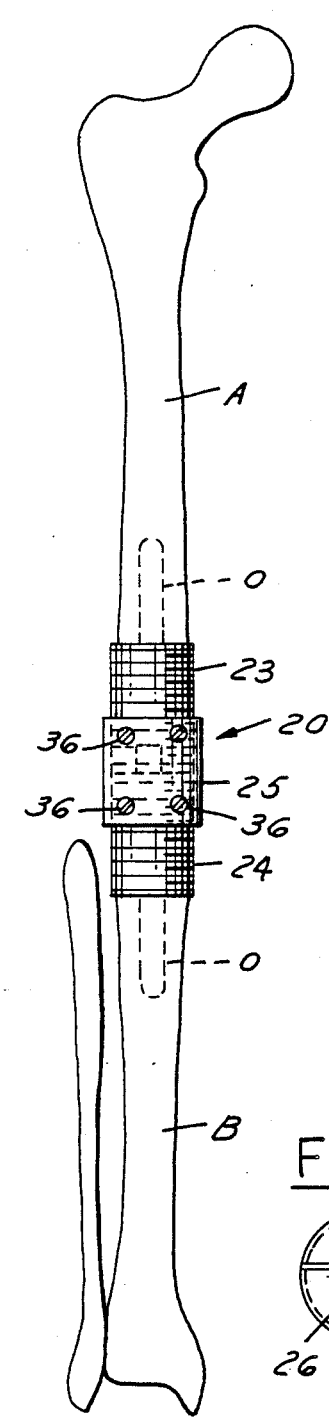
FIG. 2 is a diagrammatic view of the leg shown in FIG. 1 with bone portions removed and the bridging device embodying the invention in place.
Figure 3:
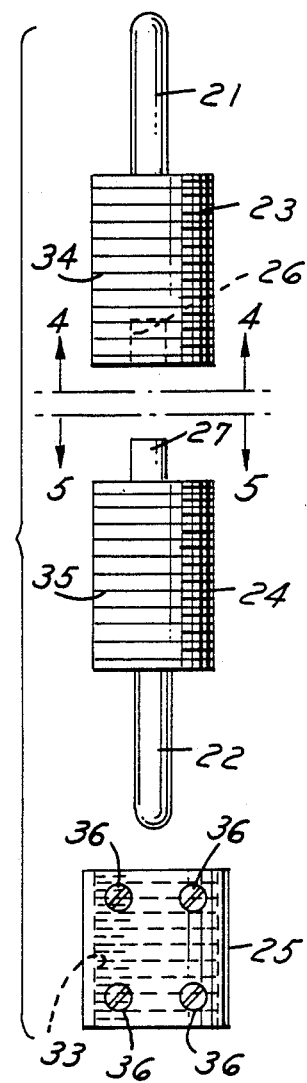
FIG. 3 is an exploded view of the bridging device.

Referring to FIG. 1, the invention relates to bridging the large gap between remaining bone portions A, B where large portions P of bone must be removed as in the case of cancer of the knee. In accordance with the invention, a bridging device 20 is utilized and comprises pin members 21,22 which include enlarged heads 23,24 that interengage one another to prevent rotational movement and a collar 25 which telescopes over the heads 23,24 to lock the pin members 21,22 against relative axial movement. The pin members 21, 22 and collar are preferably made of surgical stainless steel or titantium.

Figure 4:
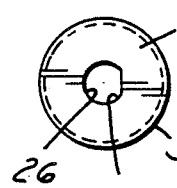
FIG. 4 is a view taken along the line 4—4 in FIG. 3.
Figure 5:
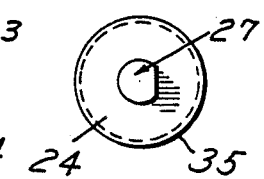
FIG. 5 is a plan view taken along the line 5—5 in FIG. 3.

As shown in FIGS. 4 and 5, opposed surfaces of heads 23,24 are formed with interengaging members 26,27 which can only interengage in one position and in this form comprises non-circular recess and projection. In the form shown in FIGS. 4 and 5, the interengaging members comprises a non-circular D-shaped and recess 26 complementary D-shaped projection 27.

Figure 7:
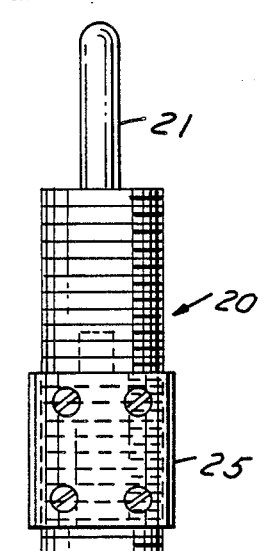
FIG. 7 is an elevational view of a bridging device embodying the invention.
Figure 8:
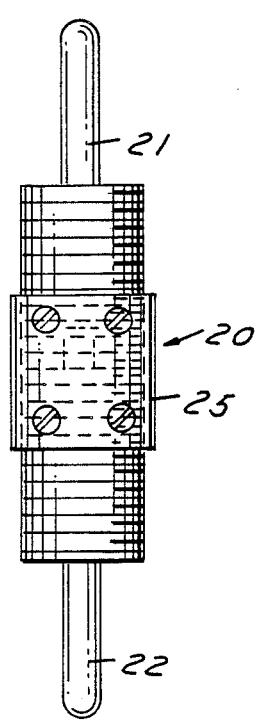
FIG. 8 is an elevational view of a bridging device embodying the invention in locked position.

In use after the bone portions are removed, tapered openings O are formed in the remaining bone portions in axial alignment. The respective pin members 21, 22 are then placed in the openings O with the use of bone cement. The collar 25 is threaded on one of the pin members. The surfaces of the pins may be roughened. Before the cement hardens, the pin members 21, 22 are rotated to bring the interengaging members 26, 27 into axial alignment (FIG. 7). The collar 25 is then rotated to cause the threads 33 of the collar to engage the threads 34 on the other pin member 21 thereby fixing the pin members 21, 22 against axial movement (FIG. 8). Set screws 36 are then tightened to lock the collar in position.

Figure 6A:
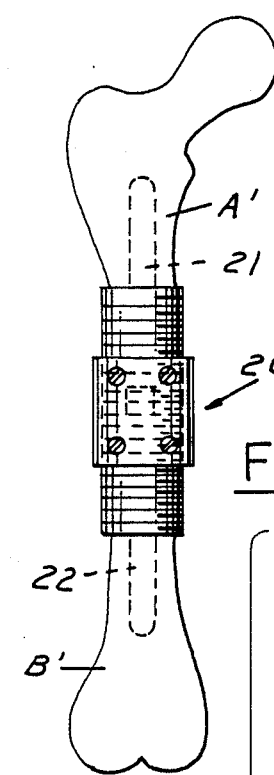
FIGS. 6 and 6a are elevational views showing the use of a bridging device on another portion of the leg.
Figure 6:
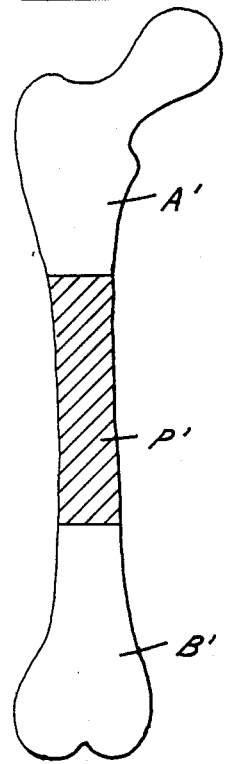

As shown in FIGS. 6 and 6A, a similar procedure can be used in another portion of the leg, as for example, in the upper leg.

Figure 9:
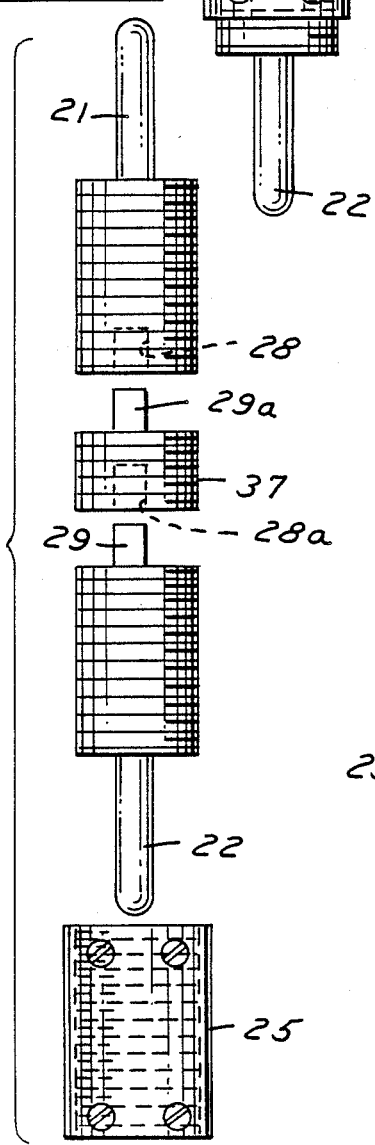
FIG. 9 is an exploded view of a modified device.
Figure 9A:
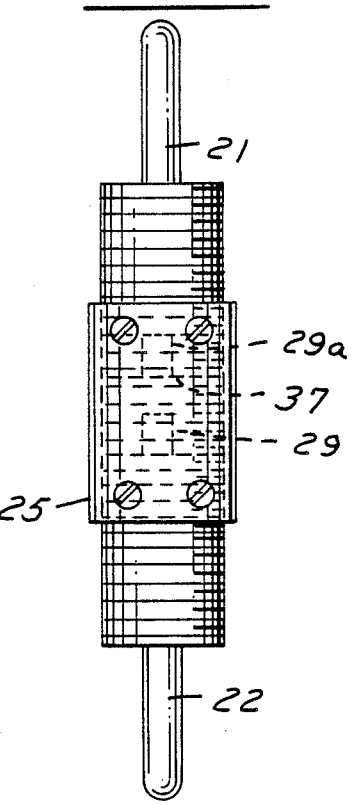
FIG. 9A is an assembled view of the device shown in FIG. 9.

Referring to FIGS. 8 and 9, the device can be lengthened by using spacer inserts 37 having an interengaging recess 28a and projection 29a thereby lengthening the device. The collar 25 then locks the pin members 21, 22 and the insert 37 against relative axial movement.

Figure 10:
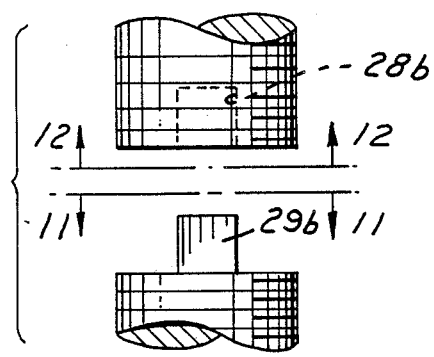
FIG. 10 is a fragmentary elevational view of another modified device.
Figure 11:
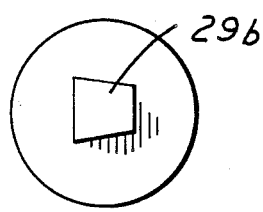
FIG. 11 is a view taken along the line 11—11 in FIG. 10.
Figure 12:
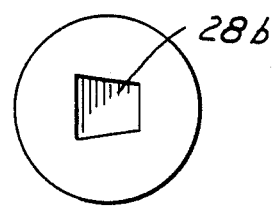
FIG. 12 is a view taken along the line 12—12 in FIG. 10.

In the form shown in FIGS. 10-12, the interengaging means comprises an axial trapezoidal shaped recess 28b and a complementary trapezoidal shaped projection 29b.

Figure 13:
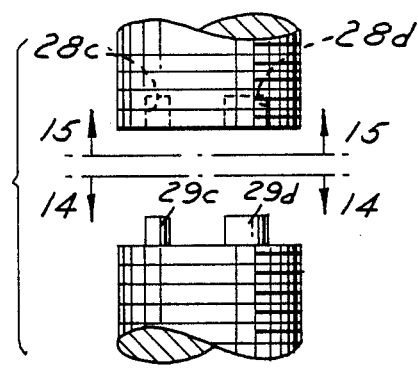
FIG. 13 is a fragmentary elevational view of another modified form of a device.
Figure 14:
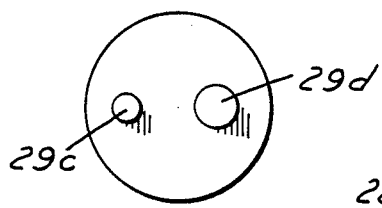
FIG. 14 is a view taken along the line 14—14 in FIG. 13.
Figure 15:
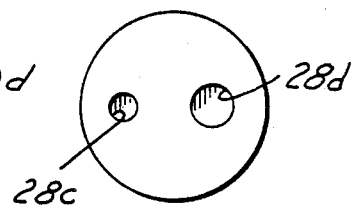
FIG. 15 is a view taken along the line 15—15 in FIG. 13.

In the form shown in FIGS. 13-15, the interengaging means comprises cylindrical recesses 28c and 28b having different diameters and are spaced from the axis which are engaged by complementary cylindrical projections 29c, 29d, respectively.

Figure 16:
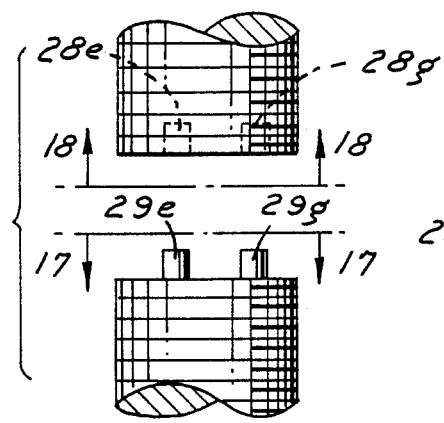
FIG. 16 is a fragmentary elevational view of another modified form.
Figure 17:
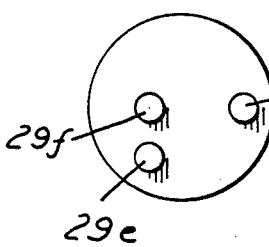
FIG. 17 is a view taken along the line 17—17 in FIG. 16.
Figure 18:
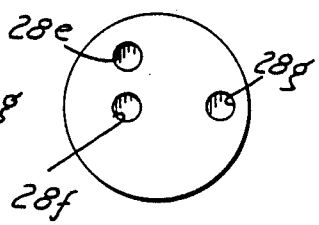
FIG. 18 is a view taken along the line 18—18 in FIG. 16.

In the form shown in FIGS. 16–18, the interengaging means comprise three cylindrical recesses 28e, 28f, 28g which are asymmetrically positioned with respect to the axis have the same diameter and are engaged.

In the form shown in FIGS. 19–21, the interengaging means comprises axially aligned recess 41 in pin member 21a and projection 42 on pin member 22a. In addition, the end of pin member 21a is formed with a semi-cylindrical recess 43 and a semi-cylindrical projection 44 while the member 22a is formed with complementary projection 45 and recess 46 which engage the recess 43 and projection 44 bringing the threads into registry when the parts are engaged. In this form, a portion of the body as at 47 and 48 is provided without threads forming a smooth surface for engagement by the screws 49, 50. In addition, each member 21a, 22a is formed with a flange 51, 52 at the base of the pin portion providing a broader area for engagement with the bone. The length of the collar 25a is greater than the axial length of the combined threads 34, 35 so that when the bridging device is assembled, none of the threads on the heads extend beyond the collar.

It has been found that the use of the bridging devices embodying the invention effectively obviate the need for amputation of the limb and provide sufficient strength for supporting the weight of the person thereby permitting self sufficiency.

I claim:

1. A bone gap bridging and fusing device for use where large portions of the bone are removed in limbs comprising first and second pin members adapted to be placed in axial opening formed in the opposed remaining bone portions, each pin member including an enlarged head on one end of the pin member having an outer surface adjacent the pin for engaging the end of the bone having an axial opening therein and an inner planar contacting surface, the inner planar contacting surfaces on the inner ends of said first and second pin members facing one another and being adapted to abut one another, each head having threads on the periphery of said head and extending in the same direction, said inner planar contacting surfaces of said first and second pin members having at least two axially extending projections on said inner surface of said first member and at least two complementary recesses on the said inner surfaces of said pin member, said projections and recesses being axially engageable by axial movement only and being fully engaged when the inner contacting surfaces of said heads are in abutting relation and being constructed and arranged to prevent relative rotation between said pin members, the lengths of said projections and recesses being such that they can be axially engaged when the pin members are placed in axial openings in opposed remaining bone portions, the remaining portions of said inner contacting surfaces of said first and second pin members being in abutment when said projections and recesses are in engagement, said threads on each said head extending to the inner contacting surface thereof and said projections and said recesses being constructed and arranged to orient said heads circumferentially to when said projections and recesses are engaged such that said threads are aligned to form a continuous thread, a collar having internal threads threaded onto the threads of said heads thereby fixing said first and second pin members against axial movement.

2. The bridging device set forth in claim 1 wherein said recesses and projections comprise at least two cylindrical recesses and at least two cylindrical projections.

3. The bridging device set forth in claim 2 wherein each said set of said recesses and projections have different diameters than other sets.

4. The bridging device set forth in claim 2 wherein said recesses and projections have the same diameters and are asymmetrically positioned on the heads.

5. The bridging device set forth in claim 1 including means between said collar and said heads for locking said collar against rotational movement relative to said pin members.

6. The bridging device set forth in claim 1 wherein the axial length of said threads on said heads is less than the axial length of said collar such that none of said threads extend beyond said collar.

7. The bridging device set forth in claim 1 wherein each of said heads includes a radial flange on the outer end of each head providing a larger surface for engagement with the bone.

8. The bridge device set forth in any of claims 1, 2, 4, 5, 7 wherein said heads have smooth portions thereon for engagement and screws extending through said collars when said heads are in abutting relation for preventing relative rotation of the collar with respect to said head.

* * * * *